(12) United States Patent
Nix et al.

(10) Patent No.: US 6,283,921 B1
(45) Date of Patent: Sep. 4, 2001

(54) ULTRASONIC VISUALIZATION AND CATHETERS THEREFOR

(75) Inventors: Elvin Leonard Nix, Putney; Amit Kumar Som, New Southgate; Martin Terry Rothman, London; Andrew Robert Pacey, Stevenage, all of (GB)

(73) Assignee: Intravascular Research Limited, Isleworth (GB)

( * ) Notice: Subject to any disclaimer, the term of this patent is extended or adjusted under 35 U.S.C. 154(b) by 0 days.

(21) Appl. No.: 09/214,739

(22) PCT Filed: Jun. 16, 1997

(86) PCT No.: PCT/GB97/01612
§ 371 Date: Jan. 11, 1999
§ 102(e) Date: Jan. 11, 1999

(87) PCT Pub. No.: WO98/02096
PCT Pub. Date: Jan. 22, 1998

(30) Foreign Application Priority Data

Jul. 11, 1996 (GB) .................................................... 9614605

(51) Int. Cl.[7] ........................................................ A61B 8/00
(52) U.S. Cl. ................................................ 600/466; 600/467
(58) Field of Search .................................. 600/447, 460, 600/462, 466, 467, 470, 468

(56) References Cited

U.S. PATENT DOCUMENTS

| 4,856,529 | 8/1989 | Segal . | |
|---|---|---|---|
| 5,279,546 | 1/1994 | Mische et al. . | |
| 5,327,885 | * 7/1994 | Griffith | ................................. 600/470 |
| 5,360,007 | * 11/1994 | Shinomura et al. | .................. 600/447 |
| 5,438,997 | * 8/1995 | Sieben et al. | ......................... 600/462 |

FOREIGN PATENT DOCUMENTS

| 0659387 | 6/1995 | (EP) . |
|---|---|---|
| 0671221 | 9/1995 | (EP) . |
| 2287375 | 9/1996 | (GB) . |
| WO8904143 | 5/1989 | (WO) . |
| WO9114401 | 10/1991 | (WO) . |
| WO9203095 | 3/1992 | (WO) . |
| WO9211809 | 7/1992 | (WO) . |
| WO9407418 | 4/1994 | (WO) . |
| WO9417734 | 8/1994 | (WO) . |

* cited by examiner

*Primary Examiner*—Marvin M. Lateef
*Assistant Examiner*—Martin Patel
(74) *Attorney, Agent, or Firm*—Richard M. Goldberg

(57) ABSTRACT

A catheter is provided that has both an ultrasonic transducer array (2) and a inflatable balloon (12) mounted at or near its distal end. A sheath catheter having a transducer array and associated multiplexer (4) arrangement located substantially coaxially within it. Furthermore, a guidewire (8) catheter having an ultrasonic transducer array mounted on it distal end.

25 Claims, 12 Drawing Sheets

US 6,283,921 B1

ULTRASONIC VISUALIZATION AND CATHETERS THEREFOR

BACKGROUND OF THE INVENTION

The present invention relates to ultrasonic visualisation and catheters therefor.

The present invention relates generally to the field of ultrasonic imaging intravascular ultrasound imaging or IVUS in transluminal coronary angioplasty known as PCTA.

In a previously proposed 5 French IVUS device having an annular array of piezo-electronic transducers at its distal end, the array which could comprise sixty-four transducer elements is about 1.6 mm in diameter. In this arrangement the transducer elements were excited in pairs thus necessitating thirty two interconnections and given the size of the catheter outer body, it was possible to route four eight-way ribbon cables within it.

When designing such a catheter with dimensions less than 5 French problems relating to the greatly reduced diameter and thus available space for interconnections are encountered. Excitation signals from an external separate apparatus are routed through a small number of interconnections (for example ten) to individual transducer elements through the use of flip-chip-bonded multiplexers positioned at the distal end of the catheter and proximally to the transducer array. A method of manufacturing the transducer array and associated multiplexers is disclosed in our copending published UK Patent Application No. 2.287,375 in which the assembly is first formed in the flat and then wrapped into a substantially cylindrical configuration. More particularly, the flat assembly comprises the transducer array, the multiplexer chips, electrically conducting multiplexer chips, electrically conducting leads and a suitable matching layer. The use of the multiplexer chips which act as electronic switches permits the use of fewer interconnections which can thus fit into a smaller lumen. In conventional PCTA an incision is made in the femoral region of the patient's leg to introduce a mid-length sheath having a diameter of typically 8 French or 2.66 mm into the femoral artery. A much thinner guide wire (typically 0.014 inches or 0.356 mm diameter) is then introduced via the resulting opening and is manually guided right up to the exact location of the affected region. The affected regions of the coronary arteries follow a tortuous route and the cardiologist relies upon the rigidity of this wire to guide it into place.

Once the end of the guide wire arrives at the required location it is kept firmly in place and in current PCTA/IVUS applications the cardiologist next has to go through an involved procedure of inserting further guide catheters, or sheath catheters prior to finally introducing the IVUS or other treatment catheter.

Keeping the guide wire firmly fixed, a guide catheter of similar dimensions to the mid-length sheath is then inserted over the guide wire, the mid-length sheath still being in place and manually guided through the opening of the aorta stopping a short distance into the coronary artery. There are various versions of guide catheters which usually have the distal ends gently curved or looped depending upon their ultimate destination within the artery system. Contrast opaque dye is then pumped through the guide catheter to flush through the aortic system rendering the cardiac vessels visible on the fluoroscope monitor to enable the cardiologist to visualise the situation.

The device catheter has a central lumen whose diameter is slightly larger (typically 0.017 inches or 0.43 mm) than that of the guide wire. This time, keeping the guide-wire/guide-catheter assembly firmly in place, the device catheter is fed over the guide wire and is simply pushed up the guide wire through the guide catheter.

The progress is monitored by noting the location of an X-ray opaque marker on the moving device catheter relative to the X-ray opaque marker on the fixed guide catheter. When the two markers are coincident the cardiologist knows that the calcified region of interest has been reached. If a balloon catheter is being used saline solution may now be pumped into the balloon to inflate it thereby dilating the affected artery. The results of the procedure are then examined using the imaging device.

The disadvantage of this known system is the inconvenience of having to withdraw one catheter and insert another in order to swap between the PCTA or other treatment procedure and the imaging procedure.

SUMMARY OF THE INVENTION

The flexible transducer design permits the possibility of mounting radially thin ultrasound arrays onto catheter configurations that can be used to simplify the swapping between procedures, and the present invention is concerned with these catheter configurations.

Published International Patent Application No. WO94/17734 (PCT/US94/00474) incidentally discloses a catheter arrangement in which a balloon is mounted distal of an ultrasonic transducer array. However, this patent application is actually concerned with overcoming the problem of the mutually incompatible performance requirements for the backing layer of the transducer array on the one hand and for the carrier of the associated electronic components on the other hand, particularly when the material of the transducer array comprises lead zirconate titanate (PZT). It is not concerned with the same problem addressed by the present invention.

Published lnternational Patent Appln. No. WO 89/04143 (PCT/US/88/04036) also discloses a catheter arrangement having a balloon and ultrasonic transducer array mounted at or near the distal end of the catheter.

A first aspect of the present invention relates to the design and manufacture of a catheter which has both a wrapped acoustic tip according to our UK Patent Application 2,287,375 and an angioplasty balloon, the acoustic tip being located distal to the balloon.

A second aspect of the present invention relates to the manufacture of a 5-6French or a 8-9French sheath catheter having a wrapped acoustic tip (according to our UK Patent Application No 2,287,375) within its body. The resultant combined sheath and transducer array catheter may be used in conjunction with current commercially available 2.9French or 5.0French balloon catheters respectively for angioplasty and stent delivery purposes or with atherectomy devices such as a Rotoblator (Registered Trade Mark) which could be inserted into the sheath catheter of the present invention.

A third aspect of the present invention relates to the combination of a wrapped acoustic fixed array transducer mounted on a guide wire which could be 0.0 14 inches in diameter to provide a 1 French catheter to produce what may be referred to as a guide-wire catheter. One key feature of this third aspect of the present invention is the manner in which the 0.014 inch dimension is maintained throughout the entire length of the catheter thus permitting device interchange during PCTA procedures with minimal disruption. The invention also reduces the number of electrical interconnections which in the specific embodiment are four.

How the invention may be carried out will now be described by way of example only and with reference to the accompanying drawings in which:

DETAILED DESCRIPTION

Figure 1:
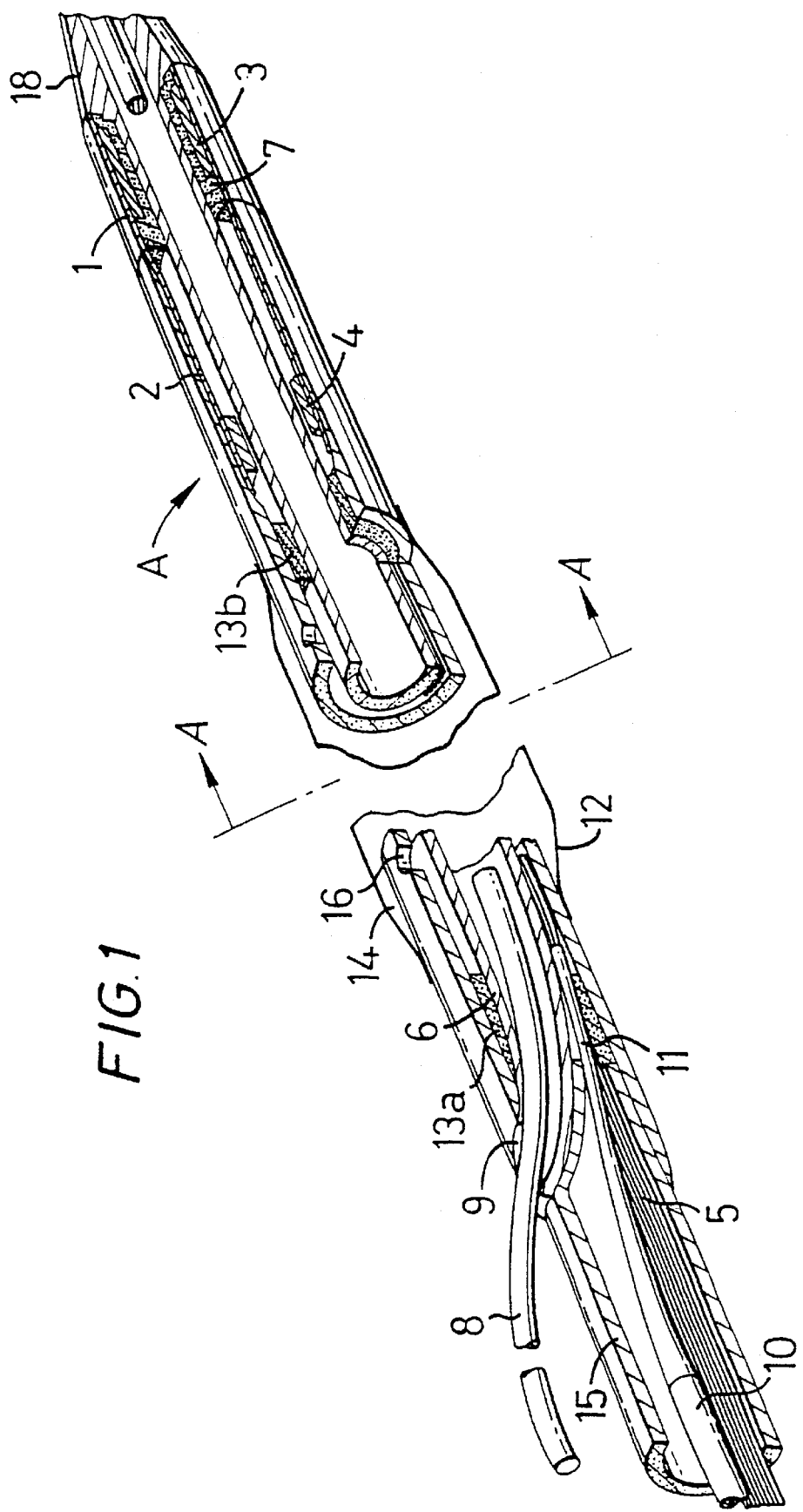
FIG. 1 is a perspective, fragmentary cut-away view of the distal end of a catheter assembly of one embodiment according to a first aspect of the invention.
Figure 2:
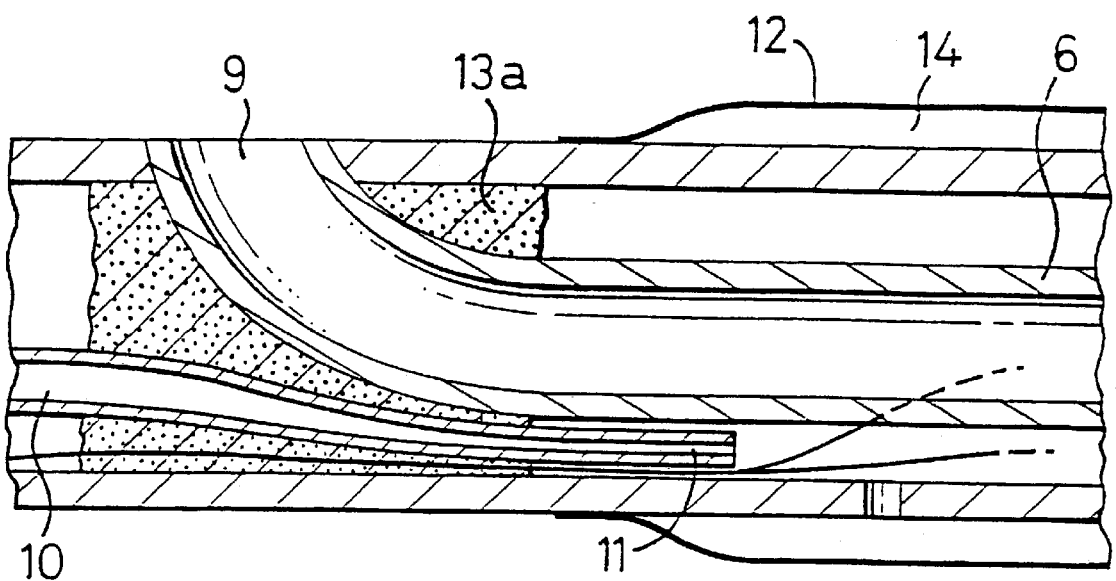
FIG. 2 is a longitudinal fragmentary sectional view of part of the assembly shown in FIG. 1.
Figure 3:
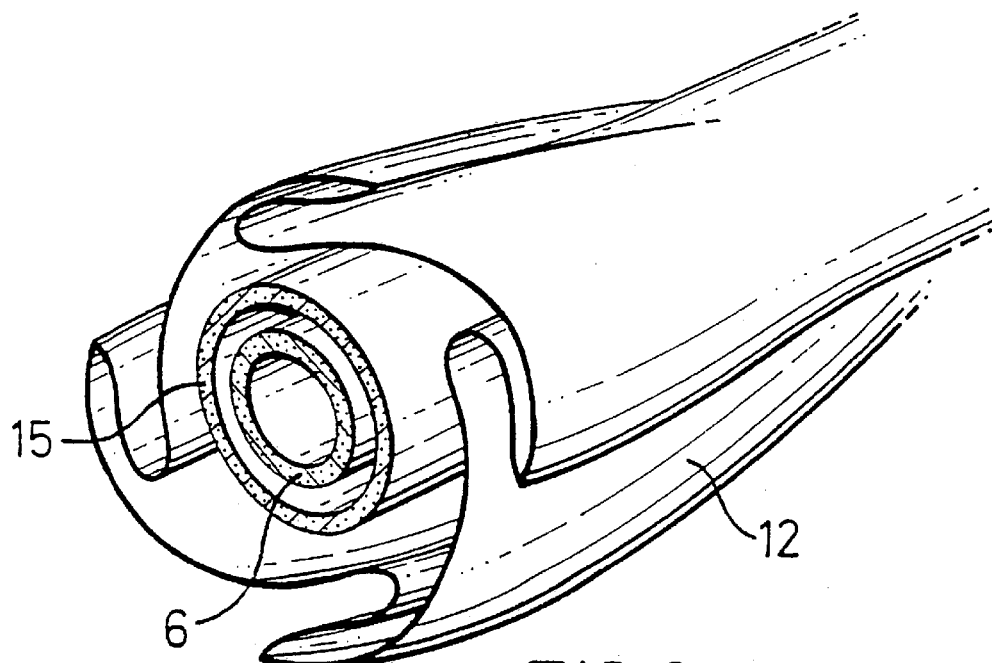
FIG. 3 is a fragmentary sectional perspective view taken on the line 3—3 of FIG. 1 and showing the balloon element of the catheter assembly shown.

FIGS. 1 to 3

The distal end of a catheter assembly is generally indicated at A in FIG. 1. The catheter has an acoustic tip 1 consisting of three major components 3, 4, 5 bonded onto a flexible polyimide substrate 2. These components comprise a micromachined PZT ultrasonic transducer array 3, four multiplexers in the form of integrated circuit chips 4 and a fourteen-way interconnect ribbon 5.

The acoustic tip 1 was originally formed in the flat and then wrapped into the form shown by the method disclosed in our published UK Patent Application No. 2,287,375. It is then mounted onto that part of the catheter referred to as inner body 6. An acoustic backing material layer 7 separates acoustic tip 1 and inner body 6.

A guide-wire 8 enters the catheter through the inner body entry point or entrance 9 of the catheter inner body 6. The guide wire 8 is fairly rigid and when inserted into the inner body entry point there is a potential for both the tip of the wire and the catheter outer body to kink. For this reason a stiffening tube 10 is provided to create an opposing and restoring force for the guide wire 8 thus maintaining the linearity of the device catheter.

The hollow stiffening tube 10 has a tapered distal end 11 and serves the dual purpose of acting as a supporting member for the guide-wire 8 and also as a lumen through which the saline solution may be pumped for inflation of a balloon 12 which is mounted on and around the catheter outer body 15.

The various components of the catheter assembly are so fused and scaled at two locations 13a and 13b that the saline solution is confined within a chamber 14 defined by the catheter inner body 6 and the outer body 15 of the catheter. The saline solution is fed first through the stiffening tube 10 into the chamber 14 and finally through a number of balloon inflation holes 16 formed on tile outer body 15 of the catheter and into the balloon cavity 14 thus inflating the balloon 12.

FIG. 2 shows a detailed longitudinal fragmentary section at the inner body entry point 9 and FIG. 3 shows how the balloon 12 is folded in its retracted condition..

The problem previously discussed in connection with the known so-called over-the-wire procedure is overcome by the use of the above-described catheter inner body 6 which consists of a short length of catheter body suitably shaped and fused into the short section of the outer body 15 of the device catheter.

The resulting cross section over the last short distal length of the catheter is that of a double-lumen structure. The advantage is that the guide wire is inside the array but only inside a short section of the rest of the catheter facilitating exchange as in known so-called rapid exchange catheters. In the catheter according to the present invention the device catheter is fed onto the guide wire 8 through the side-entry aperture 9.

In the embodiment shown in FIGS. 1 to 3 the dimensions of the various elements of the catheter are as follows:

Balloon 12: 3.5F (1.17 mm outside diameter)

Catheter inner body 6: outside diameter 0.55 mm: inside diameter 0.430 mm

Guide wire 8: diameter 0.014 inches (0.356 mm);

Catheter outer body 15: outside diameter 2.91F (0.97 mm)

Tapered tube 11: outside diameter 0.30 mm: inside diameter 0.15 mm.

FIGS. 4 to 8

Figure 4:
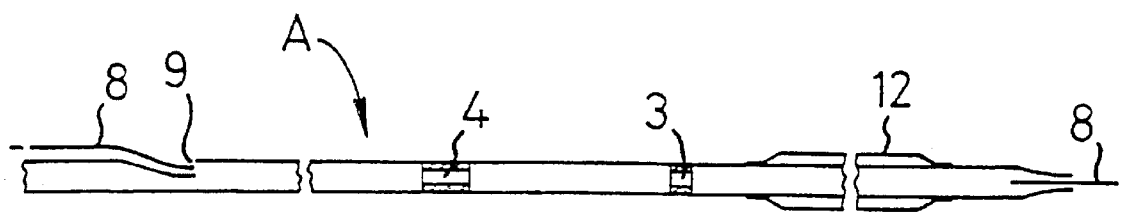
FIGS. 4 to 8 are simplified diagramatic representations of possible configurations for the type of combined catheter assembly shown in FIGS. 1 to 3.
Figure 5:
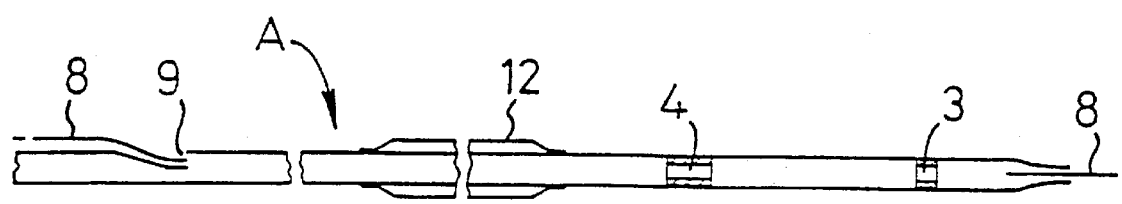

FIGS. 4 to 8 are diagrammatic illustrations of various possible embodiments in which FIG. 5 represents the arrangement shown in FIGS. 1 to 3.

In all these embodiments the slotted piezo-ceramic array 3 and the multiplexer chips 4 are shown mounted inside the outer body 15 of the catheter A with a balloon 12 mounted on the outside of it. The guide-wire 8 is shown entering the catheter via the inner body entry point 9.

In FIG. 4 the balloon 11 is positioned distal or downstream with respect to the transducer array 3 and the multiplexer arrangement 4. With this arrangement in order to get the saline solution into the balloon in the position shown it would have to be passed through the multiplexer 4 and the array 3 which could be disadvantageous given the overall dimensional restrictions. Further disadvantage is the possibility of distortion of the array by the pressure of the inflation fluid.

As indicated earlier FIG. 5 is equivalent to FIG. 1 and illustrates an embodiment where the balloon 12 is positioned between the multiplexer chips 4 and the inner body entry point 9. This is the preferred embodiment because the balloon is proximal to both the multiplexer 4 and the array 3 and they are all distal with respect to the inner body entry point 9. The balloon 12 may thus be inflated without disturbing the array 3. In addition the array 3 can have a smaller diameter than the balloon profile 12.

Figure 6:
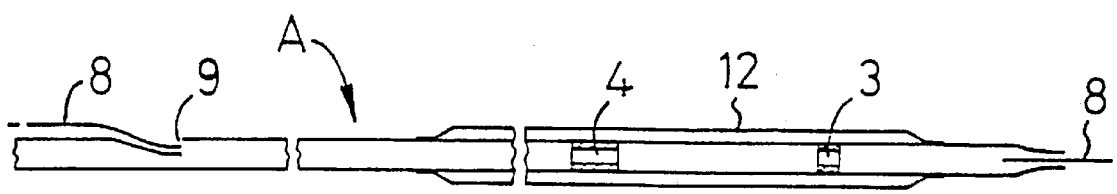

FIG. 6 illustrates an embodiment where the balloon 12 envelopes the transducer array 3 and the multiplexer chips 4. Possible array distortion during balloon inflation, and the attenuation of the ultrasound by the balloon make this a less optimal configuration.

Figure 7:
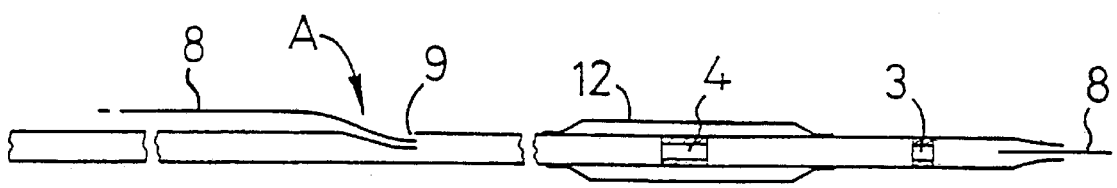

FIG. 7 illustrates an embodiment in which the key feature is that the balloon covers the multiplexer (Mux) section which is separated axially from the array without enclosing the array.

Figure 8:
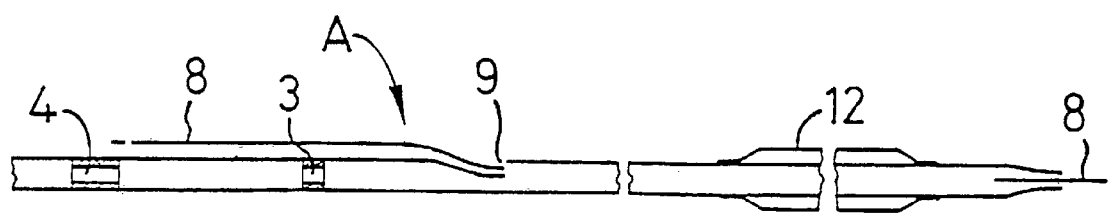

FIG. 8 illustrates an embodiment where both the balloon 12 and the inner body entry point 9 are positioned distally with respect to the transducer array 3 and multiplexer 4.

FIGS. 9 to 13

These figures illustrate an embodiment of a second aspect of the present invention.

A catheter generally indicated at B comprises a sheath catheter body 17 which carries at its distal end a cylindrical ultrasonic transducer array 3 and associated multiplexer arrangement 4 the latter being manufactured by the method disclosed in our published UK Patent Application No. 2,287,375.

Figure 9:
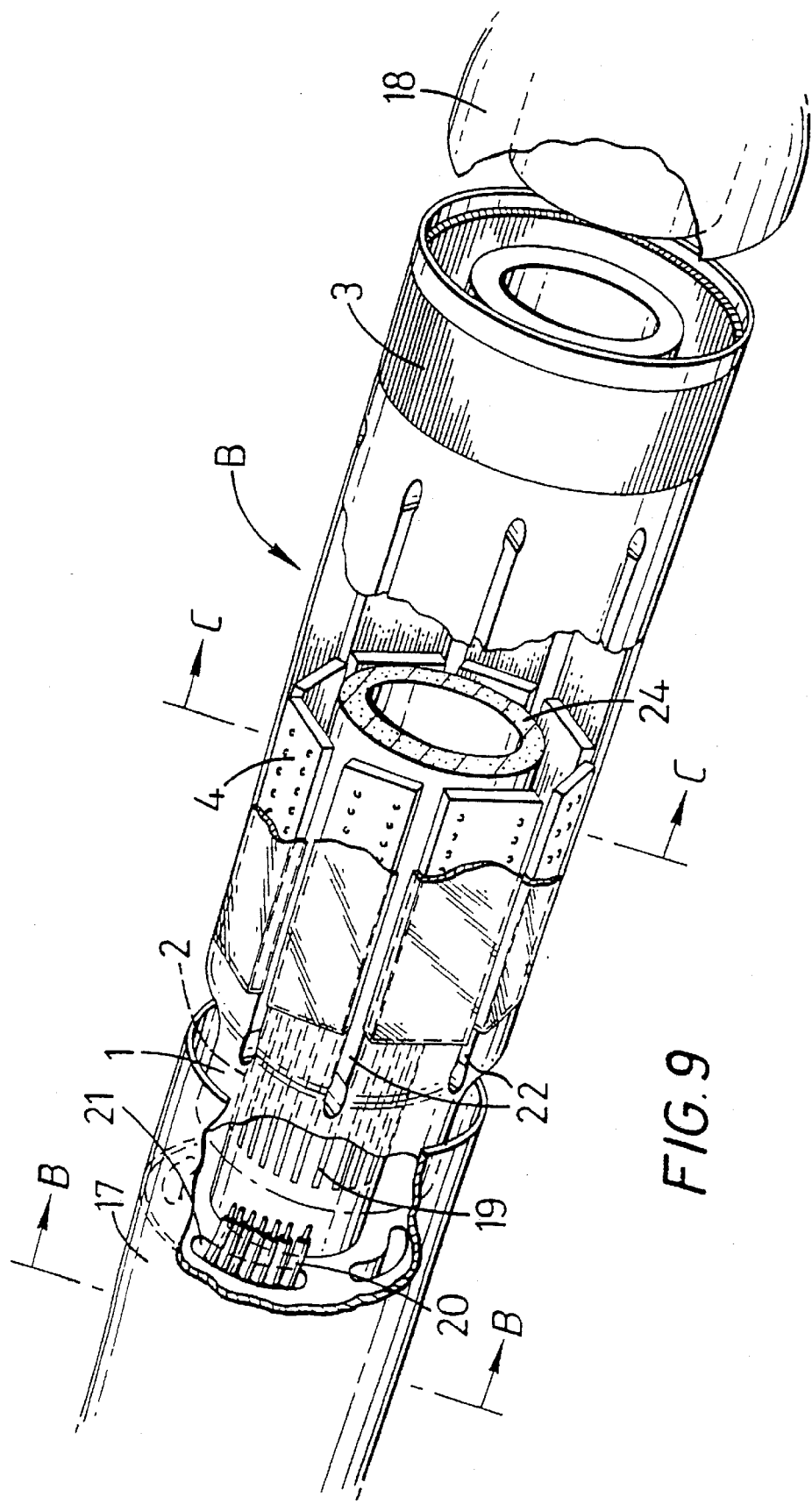
FIG. 9 is a perspective fragmentary part cut-away view of one embodiment of a catheter assembly constructed according to a second aspect of the present invention.

FIG. 9 is a view of the entire final distal assembly and it shows a flexible metallised polyimide substrate 2 with electrically conducting tracks 19 defined on one of its surfaces. Eight integrated circuits 4 forming a multiplexer arrangement are bonded onto pads defined on the substrate 2. Excited transmitted and received signals are conveyed from external electronics to and from individual sets of elements of the transducer array through four sets of miniature ribbon cables 20 fed right through the sheath catheter via four lumens 21 created within the wails of the sheath catheter 17.

There are stress relief slots 22 cut into the polyimide substrate 2 to aid in the wrapping process. The assembly is completed by the use of a soft tip 18 that enables a smooth entry into the coronary arteries to be made. The elements of the array 3 comprise precision diced piezo electric ceramic such as PZT.

Figure 10:
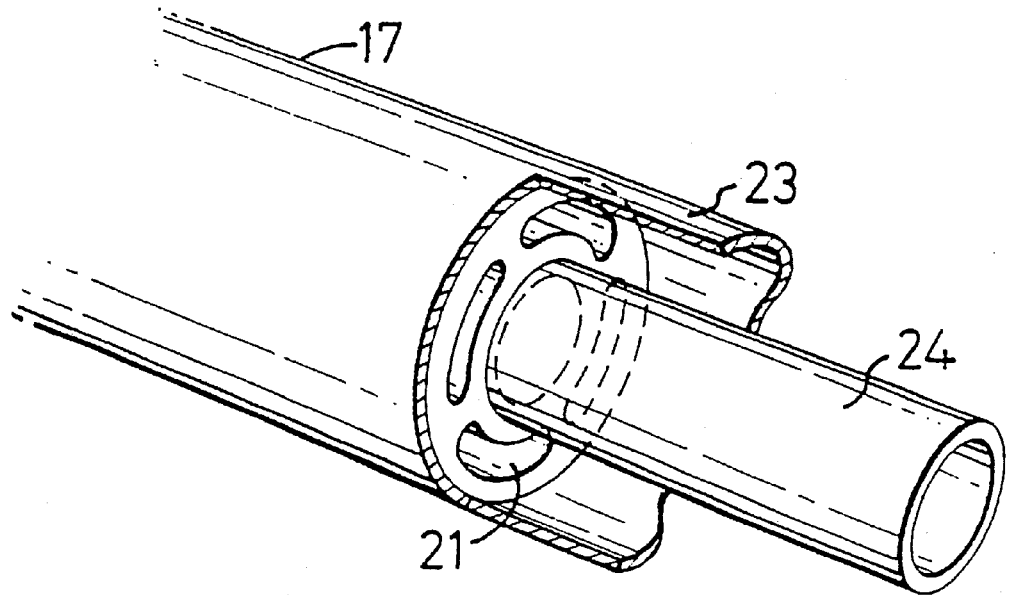
FIG. 10 is a detail of FIG. 9 but only showing the relationship between the sheath catheter and the multiplexer sheath.

FIG. 10 illustrates an outer sheath 23 which encapsulates for the multiplexer integrated circuit chips 4. A tubular body extension 24 with an inner bore of 4F is also provided and serves the dual purpose of acting as a rigid former for the fragile circuitry of the multiplexer section and as a conduit through which the device catheter (not shown) can be inserted.

Figure 11:
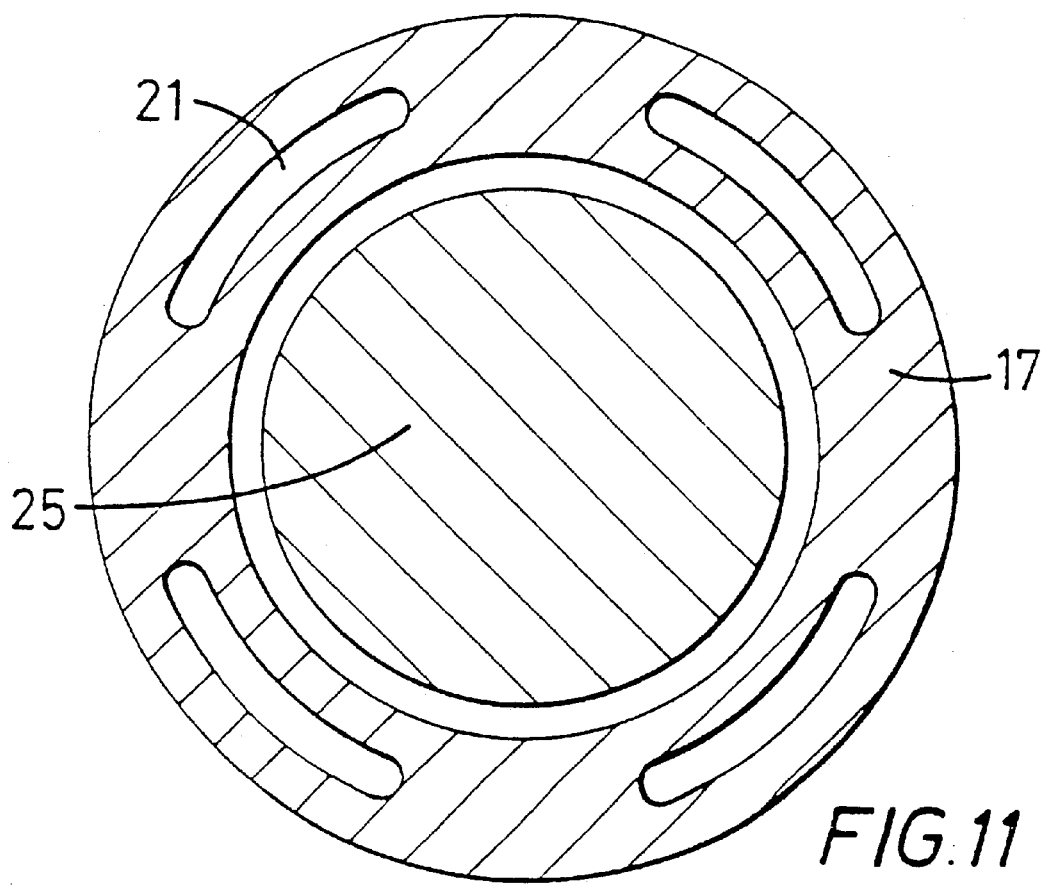
FIG. 11 is a cross-sectional view taken on the line 11—11 of FIG. 9 but also showing the device catheter.

FIG. 11 illustrates the dimensional compatibility between a sheath array catheter 17 and device catheter 25—which typically could he a balloon catheter or artherectomy device. The four thin lumens 21 extend through the entire length of the sheath catheter 17 to the imaging and processing electronics and are designed to accomodate the four ribbon cables 20 railed from the array assemble. The sheath catheter 17 could be 5-6 French with the device catheter 2.9 French. Alternatively the sheath catheter could be 8-9 French and the device catheter 5.0 French. As indicated earlier the method of manufacturing the transducer array and multiplexer arrangement is substantially as disclosed in our published UK Patent Application No. 2,287,275. In that method the transducer array and multiplexer arrangement are first fabricated in a flat configuration as shown in FIG. 12.

Figure 12:
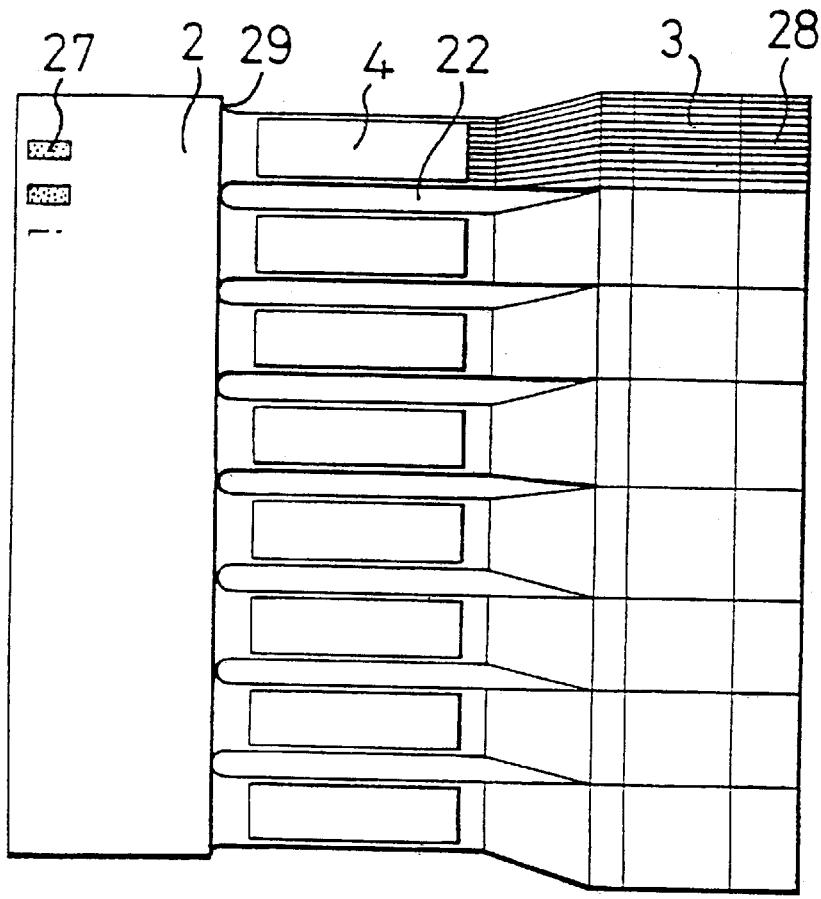
FIG. 12 is a view showing the transducer array and associated multiplexers in the flat condition.

FIG. 12 illustrates the flexible polyimide substrate 2 that has been metallised on both faces and has bonded to it a thin rectangular plate of piezo-ceramic material 3 such as PZT and eight integrated circuit chips 4 comprising a multiplexer arrangement. The multi-conductor ribbon cable 20 is not shown in FIG. 12 but is bonded onto the interconnect bond pads 27. The thin rectangular piece of piezo-ceramic material is precision diced into one hundred and twenty eight elements. There is a rectangular piece of graphite 28 that provides part of an electrical ground path. The sides of the substrate 2 are formed with a certain profile 29 which is determined by the final wrapped diameter. There are seven stress-relief slots 22 that aid in the wrapping process by making the substrate easier to form into a cylinder.

Figure 13:
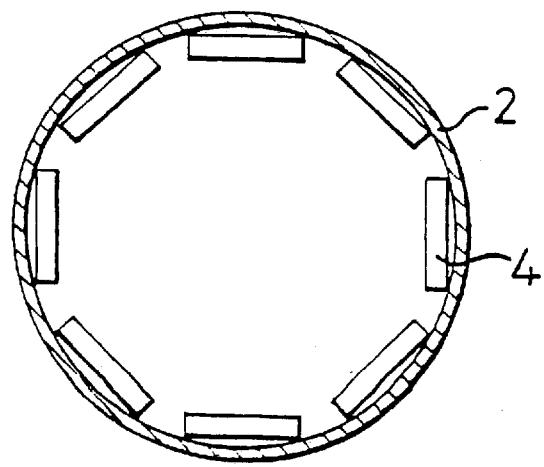
FIG. 13 is a cross-sectional view taken on the line 13—13 of FIG. 9.

FIG. 13 shows a cross section of the wrapped assembly. This cross sectional diagram, shows the relationship between the eight integrated circuit chips 4 and the resultant Surrounding cylinder of polyimide substrate 2.

Figure 14:
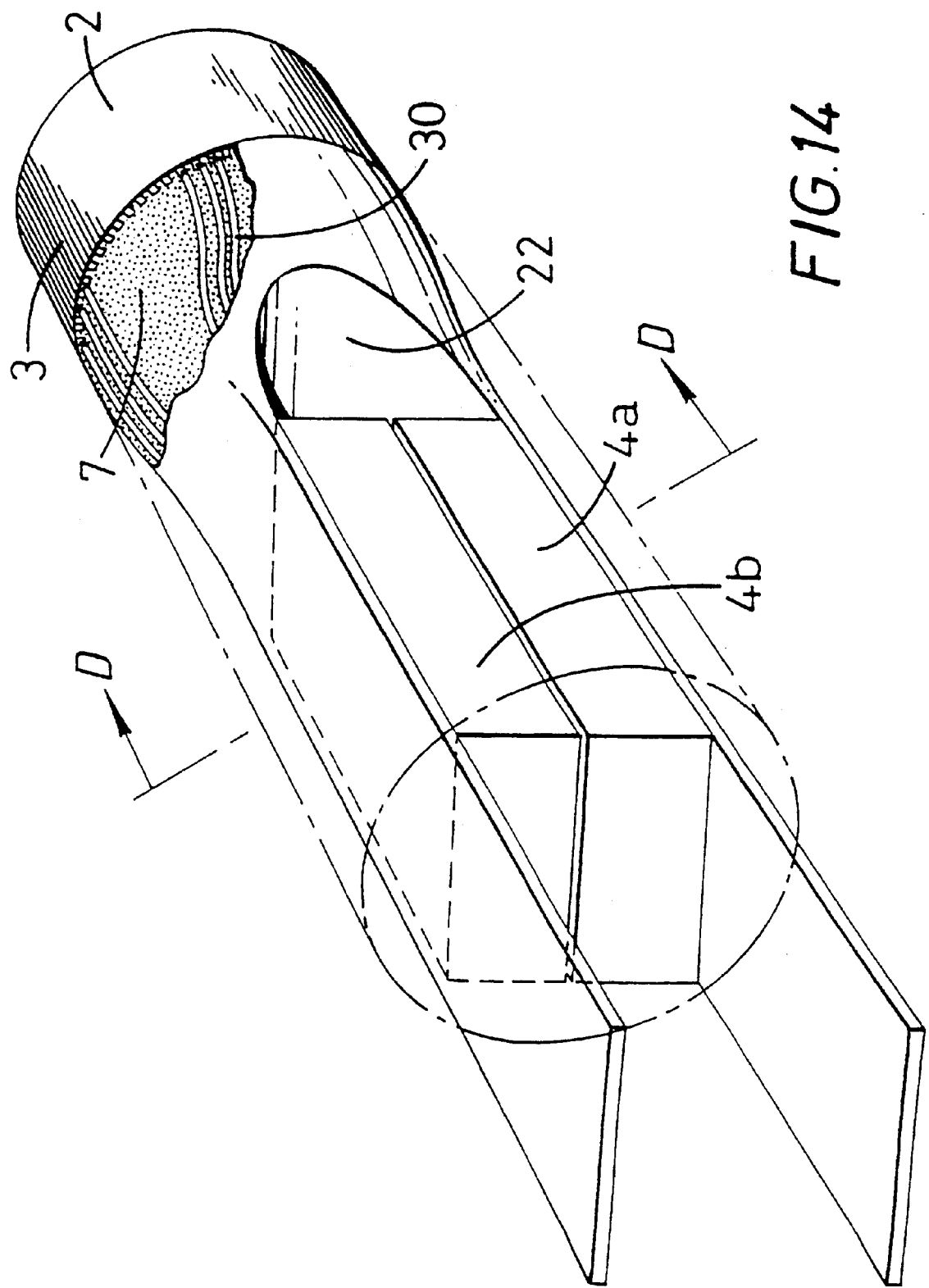
FIG. 14 is a fragmentary perspective view of one embodiment of the third aspect of the present invention.
Figure 15:
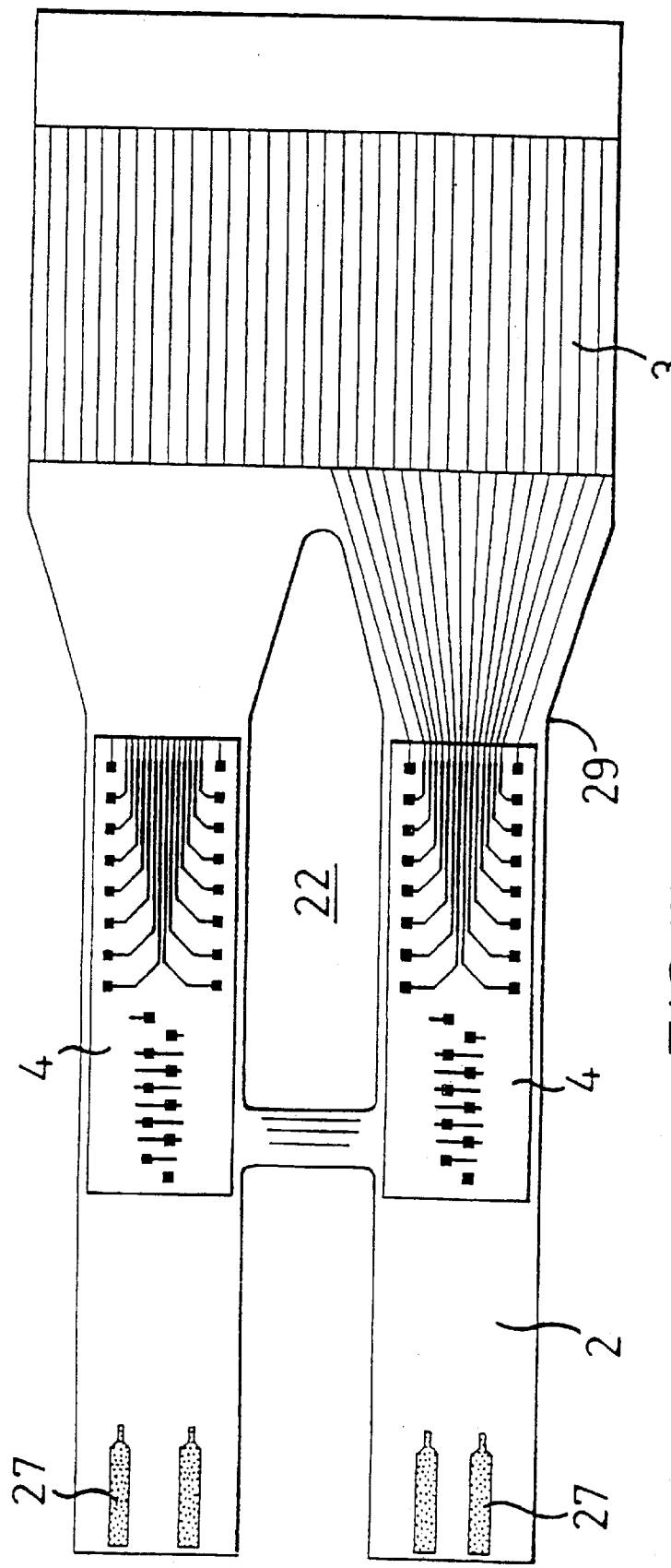
FIG. 15 illustrates the ultrasonic transducer array and associated multiplexer arrangement of FIG. 14 when in the flat configuration.
Figure 16:
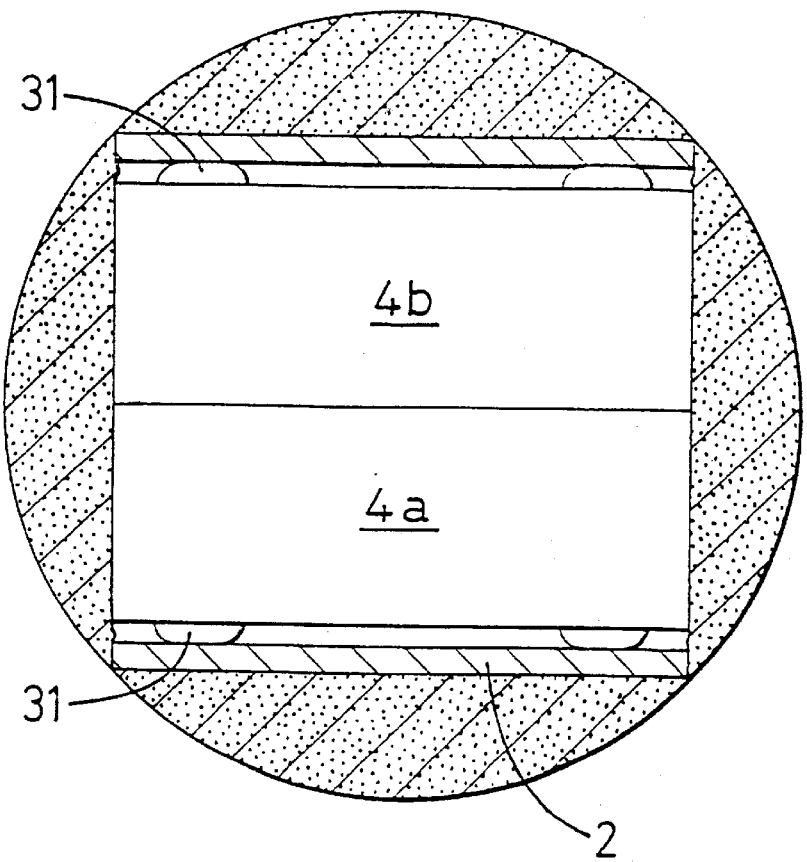
FIG. 16 is a cross-section taken on the line 16—16 of FIG. 14.

FIGS. 14 to 16

These figures illustrate an embodiment of the third aspect of the present invention which comprises a 1 French diameter catheter and an associated cylindrical ultrasonic transducer array 3 with a multiplexer arrangement 4. The multiplexer arrangement differs in configuration from that of FIGS. 1 and 9 in that it comprises two multiplexer chips 4 which are so positioned on a flexible circuit assembly 2 (see FIG. 15) that when that assembly is rolled up become positioned back-to-back with the transducer array rolled into a cylindrical configuration. The entire assembly has an outside diameter no greater than 1 French (i.e. 0.014 inches). Such a device is of the same diameter as a typical catheter guide wire and thus would not only be able to access the thinnest of coronary arteries but due to the use of on-board miniature integrated circuit switches 4, few electrical wires are involved thus keeping the body construction simple.

This leads to a low cost, single-use device. Additionally, there is no need for a lumen through the center of this device. This resulting saving in space is now available for more acoustic backing layer for the transducer array than in other designs. This thicker backing layer results in a stronger and clearer signal being generated by the transducer array which, in turn, leads to a sharper and clearer image after employing suitable image processing.

Typically guide wires are not simple wires but arc complex structures often consisting of two or more wires wound into a helix. Therefore although there is no discrete body, the term 'body' here refers to the whole assembly.

The backing layer is an ultrasound material combining high acoustic attenuation with defined acoustic impedance, consisting of a rubberised resin loaded with a suitable filler material such as tungsten powder and is a cylinder of diameter of 0.24 mm.

The device illustrated in FIG. 14 would operate at 40 MHz and have thirty two transducer elements.

Apart from the use of only two multiplexer integrated circuits 4 instead of the eight of the embodiment shown in FIG. 9 the general construction of the transducer array and associated multiplexers is substantially the same and manufactured by the general method discussed in our published UK Patent Application No. 2,287,375.

FIG. 14 shows the distal end of the guide wire catheter which has mounted on it the acoustic transducer array and associated electronics and which has a dimension of 1 F. The two multiplexers 4a and 4b are flip-chip-bonded onto fine-pitch circuitry 30 defined on the flat metallised polyimide substrate 2 are shown. As indicated earlier the flexible film has been folded in such a manner so as to bring the two chips 4a 4b in contact with and positioned back-to-back with respect to each other. The transducer array 3 is also shown in its wrapped configuration the backings material 7 injected into the volume bordered by the inner diameter of the array. Also shown on this view is one of two stress relief slots 22 cut into the polyimide material that acts to aid in the wrapping process. There are electrical interconnections which run the whole length of the catheter and are bonded onto the bond pads 27 created on the flexible circuit.

FIG. 5 shows the earlier stage in the manufacture of the device of FIG. 14 in which a circuit is fabricated in the flat on a flexible polyimide substrate 2 that has been metallised on both faces. Three principal components are bonded onto this substrate namely a thin rectangular plate of piezo-ceramic material 3, two integrated circuit chips 4 and a multi-conductor cable that is not shown but which is bonded onto the interconnect bond pads 27. The thin rectangular piece of piezo-ceramic 3 (typically PZT) is precision diced into thirty two transducer elements. The circuit is shown with a certain profile 29 that has been selected with the final wrapped diameter in mind. Also shown on the circuit is a stress-relief slot 22 that aids the wrapping process.

FIG. 16 is a cross-sectional view of the multiplexer arrangement of FIG. 14. The folded polyimide substrate 2 with fine-pitch circuitry defined on it is shown enclosing two multiplexer chips 4a and 4b. The diagram shows that if the multiplexers are designed with typical widths of approximately 0.260 mm, the entire sensor fits into the dimensions of a 0.014 inch or 1 French guidewire. The chips are flip-chip-bonded onto bond pads by reflowing solder bumps 31 that are positioned on contact pads located on the chips. In this wrapped design, the two multiplexer chips are positioned back-to-back in order to fit within the 0.014 inch diameter and may be attached to each other through the use of a suitable adhesive.

Figure 17:
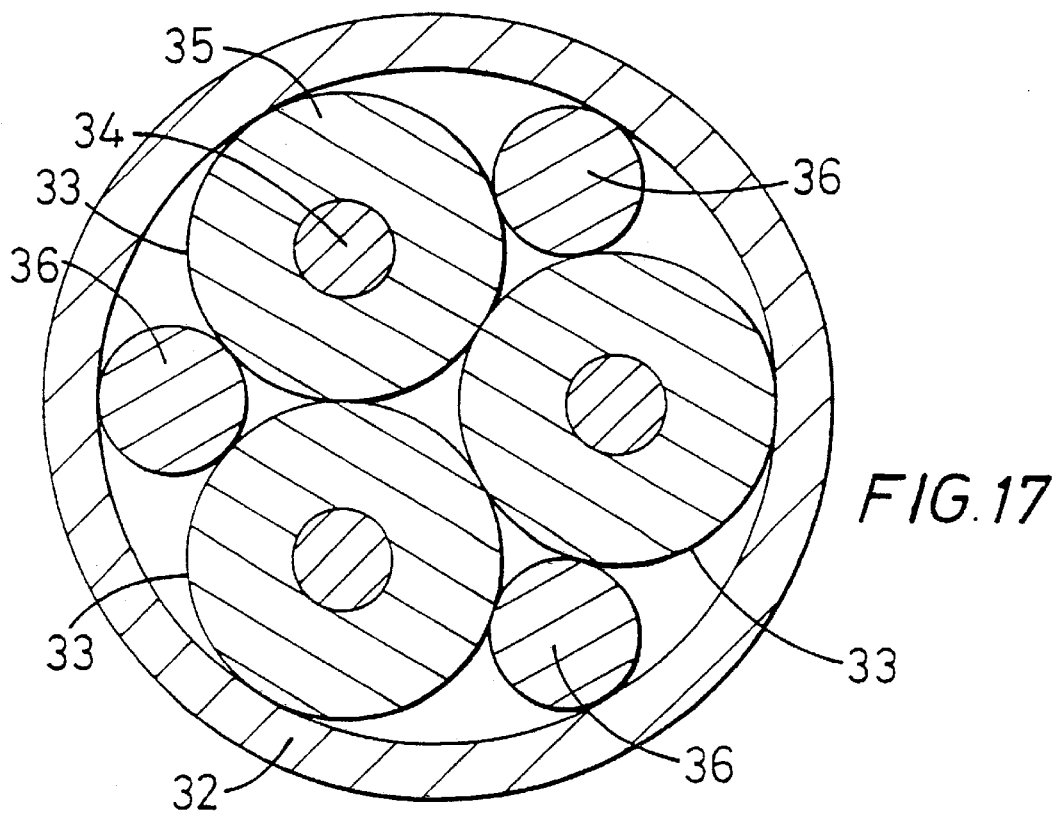
FIGS. 17 to 21 illustrate cross-sectional and perspective views of a number of body and interconnect configurations to the distal end of which the arrangement of FIG. 14 is attached.
Figure 18:
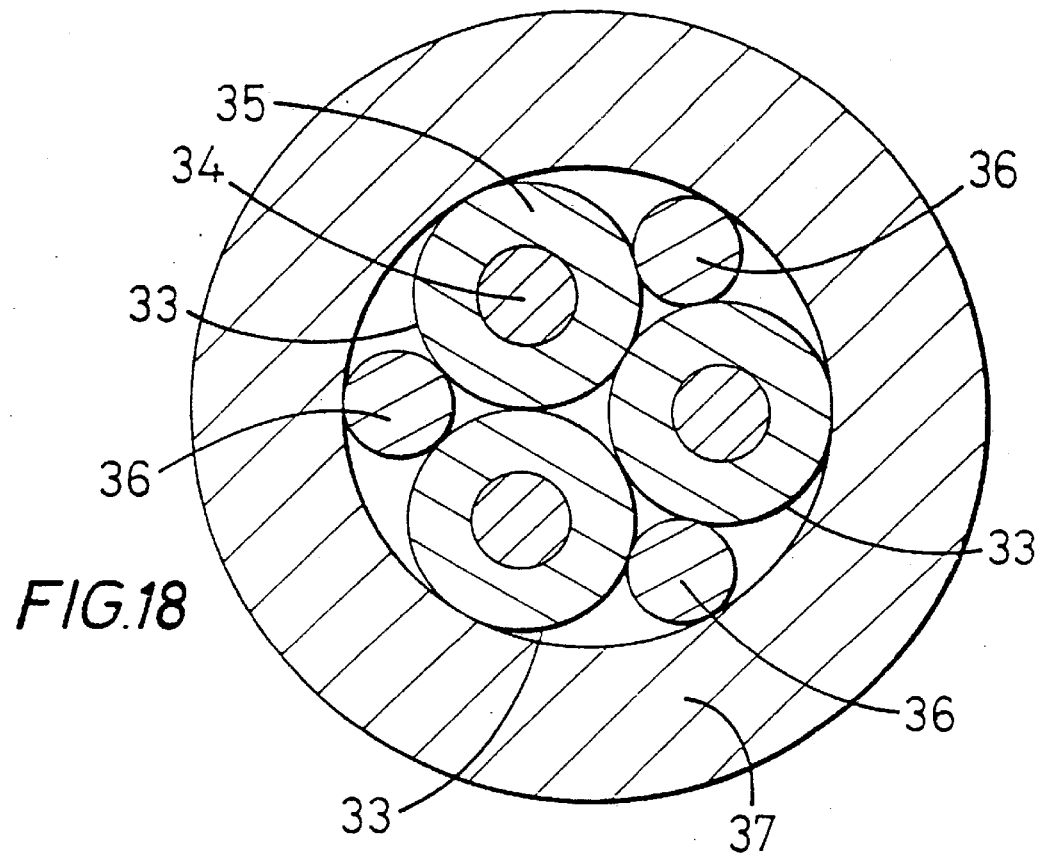

FIGS. 17 and 18

These figures illustrate five possible constructions for the body of the catheter to the distal end of which the arrangement shown in FIG. 14 is mounted. Referring to FIG. 17, a polyimide tube 32 with or without an external winding which acts as a ground return having a 1 French outer diameter contains within it three monofilaments 33 each consisting of a central copper conductor 34 (the external winding would act as a fourth conductor) with an outer dielectric jacket 35 which could be of low dielectric loss fluoropolymer. In order to maintain suitable torsional rigidity and stiffness three thin wires 36 that could be of a copper-alloy type are positioned within the remaining spaces.

Referring to FIG. 18 the body comprises a stainless steel tube 37 having a 1 French outer diameter. The tube 37 contains three monofilaments 33 each consisting of a central copper conductor 34 with an outer dielectric jacket 35 which could be of a low dielectric loss fluoropolymer.

Figure 19:
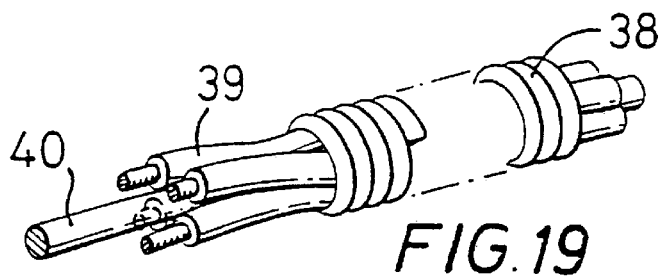
Figure 20:
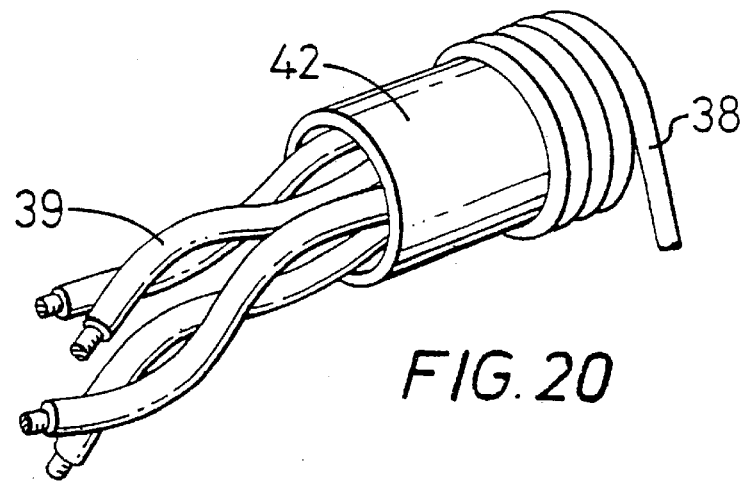
Figure 21:
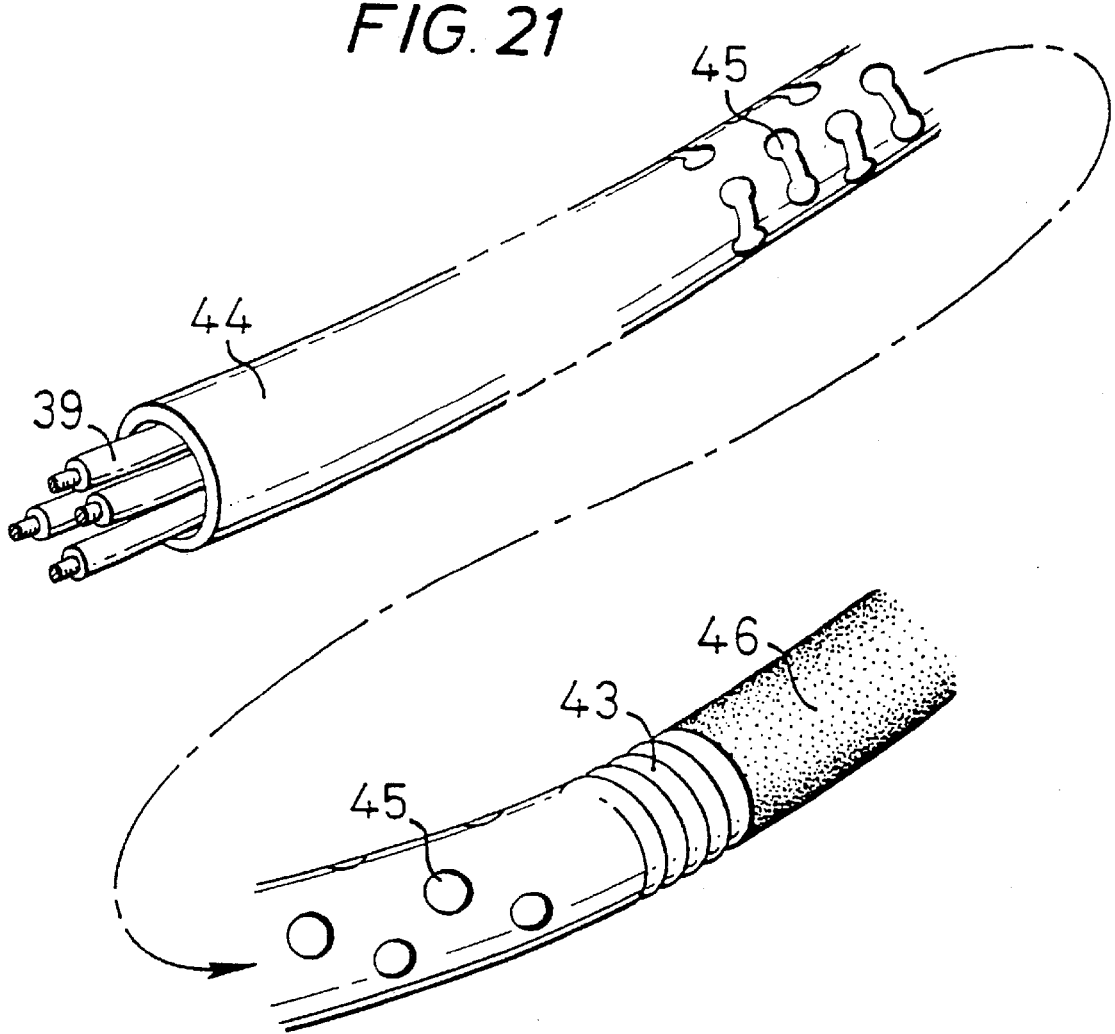

FIGS. 19 to 21

Referring to FIGS. 19 and 20 these illustrate possible body constructions which employ a steel-wire counterwinding 38 to add torsional rigidity to the assembly. In the arrangement of FIG. 19 there are four monofilament electrical conductors 39 symmetrically disposed around a central mandrel 40.

In the arrangement of FIG. 20 there are again four monofilament electrical conductors 39 but instead of the mandrel 40 there is an external tube 42 made of polyimide which contains the conductors and is reinforced in terms of torsional rigidity by the steel-wire counterwinding 38. These four monofilaments (electrical conductors 39) are configured into two twisted-pairs in order to aid in noise shielding.

FIG. 21 illustrates a variation on the constructions of FIGS. 19 and 20 in that the separate steel-wire counterwinding 38 is replaced by a functionally equivalent spiral winding 43 which is formed integrally with the wall of a thin walled stainless-steel tube 44 that is centreless ground. In order to increase the flexibility of the tube 44 it is provided with recesses or apertures 45 in its wall having shapes and/or orientations which will promote flexibility whilst allowing the tube to retain its torsional rigidity. The spiral winding 43 may be filled with a suitable resin 46 to provide greater flexibility within the tip region of the catheter. Both the apertures/recesses 45 and the spiral winding 43 may be created, for example, by using a laser or through chemical means such as etching.

Figure 22:
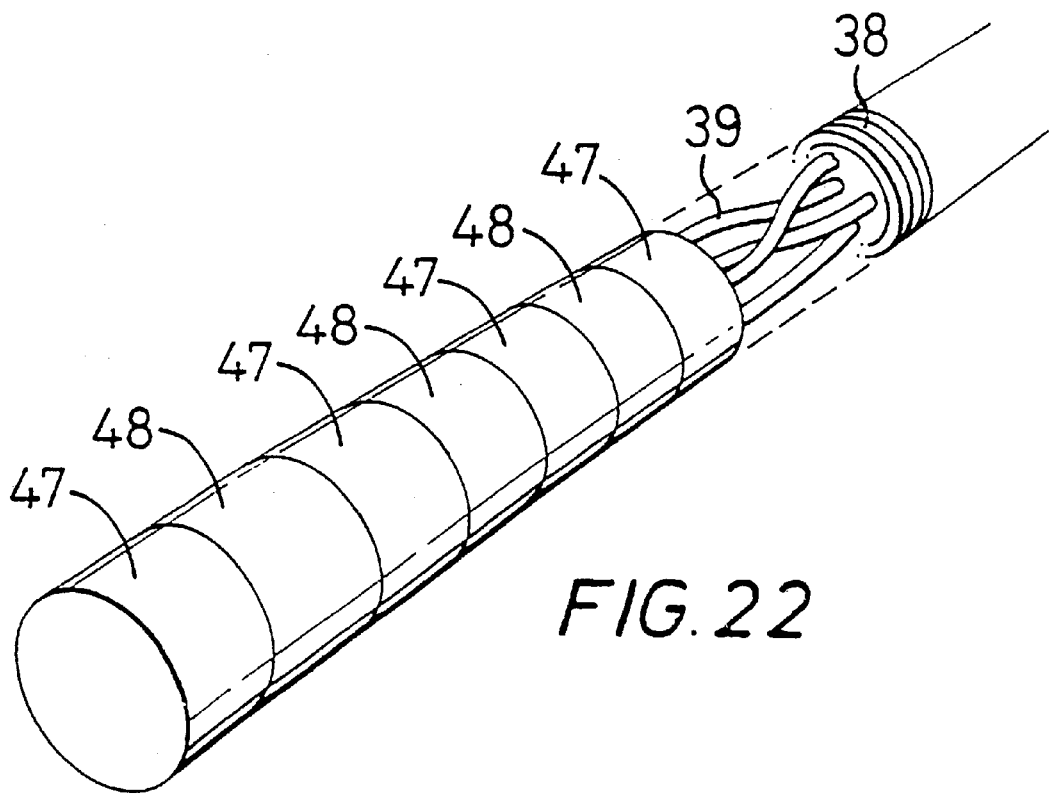
FIGS. 22 and 23 illustrate an arrangement by which the electrical connections to and from the ultrasonic transducer array and multiplexer arrangement are accomodated at the proximal end of the catheter and how the 1 French dimension is not exceeded by the proximal connector itself.
Figure 23:
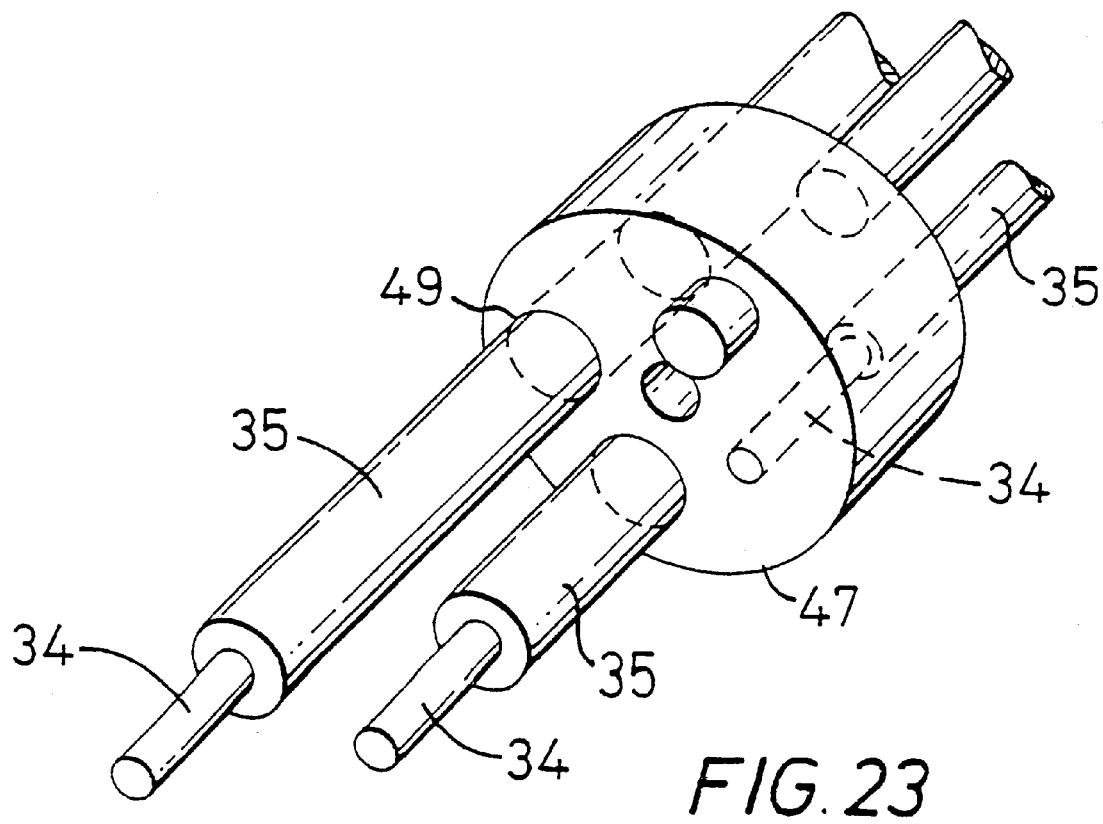

FIGS. 22 and 23

These figures illustrate what is in effect an electrical plug arrangement mounted at the proximal end of the catheter to enable it to be plugged into the external electrical/electronic equipment. The problem is that if a conventional electrical plug were used it would have too large an external diameter and prevent catheters being slid over the catheter from its proximal end.

With the arrangement illustrated the outside diameter of the plug arrangement is 1 French. Each one of the four conductors 39 extending through the length of the catheter has one conducting former 47 assigned to it. The conducting formers 47 are separated from one another by insulating formers 48. Both types of former 47 and 48 have an external diameter of 1 French thus maintaining the 0.014 inch external diameter throughout the entire length of the catheter. thus permitting the interchange of the various device catheters that may be required. These would be slid onto over and along the guide-wire catheter illustrated.

FIG. 23 shows one of the conducting formers 47 in detail where the insulating jacket 35 of one interconnect 33 has been stripped to expose the bare conductor 34. Each former 47 has four holes 49 to accommodate the interconnects 33. In each case the bare conductor 34 is inserted into its respective hole 49 and affixed within it using a suitable technique such as reflow soldering or a conductive adhesive.

Because of the axial separations of the conducting formers 47 each of the four interconnects has to be a different length to enable it to be similarly inserted through its own insulating, former 48 and into its own associated conducting former 47. The torsional counter windings 38 is suitably terminated before the first conducting former 47

Suitable adhesives are used to pot the final assembly of the four electrically separated conducting formers 47 to form a connector which is adapted to plug into a stand-alone external system for further processing of the echo signals into an image.

What is claimed is:

1. A non-rotatable catheter comprising:

an outer catheter body having a wall with an aperture in the wall, an inner catheter body located within the outer catheter body and terminating at a proximal end thereof in the aperture, an ultrasonic transducer array non-rotatably mounted on the catheter at or near a distal end of the catheter, a multiplexer arrangement, at least one of the ultrasonic transducer array and the multiplexer arrangement carried on an outer surface of the inner catheter body, and an inflatable balloon mounted on the catheter at or near the distal end of the catheter, whereby the catheter may be slid over and along a guide wire such that the distal end of the guide wire will lie substantially coaxially with the inner catheter body and the distal end of the outer catheter body.

2. A catheter as claimed in claim 1, in which the multiplexer arrangement is associated with the transducer array and is mounted on the catheter at or near the distal end of the catheter.

3. A catheter as claimed in claim 1, in which the transducer array has a diameter smaller than a diameter of the balloon.

4. A catheter as claimed in claim 2, in which the transducer array is located distal to the balloon such that the balloon covers the multiplexer arrangement, thus allowing a distal end of the balloon to be close to the transducer array.

5. A catheter as claimed in claim 1, further comprising a reinforcing tube located within the outer catheter body, with a distal end of said reinforcing tube being located adjacent to a proximal end of the inner catheter body where said proximal end of the inner catheter body meets said aperture, in order to both reinforce the inner catheter body thereat and to also act as a conduit for introduction of a fluid into the balloon to support the balloon.

6. A catheter as claimed in claim 5, in which the distal end of the reinforcing tube is tapered.

7. A catheter as claimed in claim 5, further comprising:
a fluid chamber formed between the outer surface of the inner catheter body and an inner surface of the outer catheter body, and
a fluid tight seal fluidly connecting the distal end of the reinforcing tube with said fluid chamber, to enable fluid to be introduced into said fluid chamber through the reinforcing tube.

8. A catheter as claimed in claim 7, in which the balloon is carried by and secured to an outer surface of the outer catheter body, and the outer catheter body has at least one aperture in the wall of the outer catheter body, whereby liquid in said chamber can flow into the balloon.

9. A catheter as claimed in claim 1, in which the balloon includes an elastomeric envelope of substantially elongated configuration which, in an uninflated condition, is folded around said outer catheter body so that introduction of the fluid causes the material of the balloon to unfold and adopt an inflated configuration.

10. A sheath catheter comprising:
a cylindrical sheath having a lumen for receiving a separate device catheter inserted through the lumen,
a substantially cylindrical ultrasonic transducer array located within the sheath and being substantially coaxial therewith, and
a multiplexer arrangement associated with the transducer array, said multiplexer arrangement located within the sheath and being substantially coaxial therewith.

11. A sheath catheter as claimed in claim 10, further comprising a tubular support located coaxially in said sheath catheter and within said substantially cylindrical ultrasonic transducer array and associated multiplexer arrangement, said tubular support being positioned and dimensioned to act as a support for the multiplexer arrangement.

12. A sheath catheter as claimed in claim 11, further comprising a multiplexer protecting sheath located radially outwardly of the substantially cylindrical multiplexer arrangement.

13. A sheath catheter as claimed in claim 11, in which the catheter has a wall formed with a plurality of cross-sectioned lumens for accommodating a same plurality of ribbon electrical conductors for transmitting and receiving electrical signals to and from said transducer array and associated multiplexer arrangement.

14. A catheter comprising:
a distal end,
an ultrasound transducer array mounted on the distal end of the catheter,
electrical conductors between the transducer array and a proximal end of the catheter, whereby electrical signals may be transmitted to and received from said transducer array, and
the catheter forms a guide wire having an outside diameter throughout its length equal to or less than 1 French.

15. A catheter as claimed in claim 14, further comprising a multiplexer arrangement located at the distal end of the guide wire and including two integrated circuits positioned back-to-back with respect to each other.

16. A catheter as claimed in claim 15, in which the transducer array forms a cylinder, and the cylinder is filled with an acoustic backing layer material.

17. A sheath catheter comprising:
a distal end,
an ultrasound transducer array mounted on the distal end of the catheter,
electrical conductors between the transducer array and a proximal end of the catheter, whereby electrical signals may be transmitted to and received from said transducer array,
a torsional reinforcing winding on a catheter body thereof,
the catheter forms a guide wire having an outside diameter throughout its length equal to or less than 1 French, and
a multiplexer arrangement located at the distal end of the guide wire and including two integrated circuits positioned back-to-back with respect to each other.

18. A catheter as claimed in claim 17, in which the winding is formed as an element separate from the catheter body.

19. A catheter as claimed in claim 17, in which the winding is formed as an integral part of the catheter body.

20. A catheter as claimed in claim 17, in which the catheter body is formed with apertures or recesses in a wall thereof to render the catheter body more flexible.

21. A sheath catheter comprising:
a distal end,
an ultrasound transducer array mounted on the distal end of the catheter, the transducer array having a plurality of electric cables extending substantially axially therefrom towards a proximal end of the catheter,
a plurality of disc-like electrically insulating and electrically conducting formers equal in number to the plurality of the electric cables and located in line and proximally of said electric cables, each former having a plurality of apertures therethrough to accommodate at least one of the electric cables, and each cable having a central conductor electrically connected to a unique one of said electrically conducting formers,
electrical conductors between the transducer array and a proximal end of the catheter, whereby electrical signals may be transmitted to and received from said transducer array,
the catheter forms a guide wire having an outside diameter throughout its length equal to or less than 1 French, and a multiplexer arrangement located at the distal end of the guide wire and including two integrated circuits positioned back-to-back with respect to each other.

22. A catheter as claimed in claim 1, further comprising a cylindrically tapered tip of a relatively soft material formed on a distal end of the catheter in order to facilitate insertion of the catheter into a patient's artery.

23. A catheter as claimed in claim 10, further comprising a cylindrically tapered tip of a relatively soft material formed on a distal end of the catheter in order to facilitate insertion of the catheter into a patient's artery.

24. A catheter as claimed in claim 14, further comprising a cylindrically tapered tip of a relatively soft material formed on a distal end of the catheter in order to facilitate insertion of the catheter into a patient's artery.

25. A catheter as claimed in claim 1, in which the transducer array and associated multiplexer arrangement are initially formed flat and then wrapped into a cylinder for insertion into the distal end of the outer catheter body of the catheter.

* * * * *